(12) United States Patent
Menzel et al.

(10) Patent No.: US 12,023,446 B2
(45) Date of Patent: Jul. 2, 2024

(54) METHOD AND DEVICE FOR CONTROLLING THE TEMPERATURE OF THE GAS FLOW IN MEDICAL DEVICES

(71) Applicant: W.O.M. World of Medicine GMBH, Berlin (DE)

(72) Inventors: Felix Menzel, Berlin (DE); Andreas Zeyssig, Berlin (DE); Johannes Koerner, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 926 days.

(21) Appl. No.: 15/547,291

(22) PCT Filed: Jan. 27, 2016

(86) PCT No.: PCT/DE2016/000027
§ 371 (c)(1),
(2) Date: Feb. 15, 2018

(87) PCT Pub. No.: WO2016/119773
PCT Pub. Date: Aug. 4, 2016

(65) Prior Publication Data
US 2018/0147384 A1 May 31, 2018

(30) Foreign Application Priority Data
Jan. 27, 2015 (DE) .......................... 102015000845.5

(51) Int. Cl.
*A61M 16/10* (2006.01)
*A61M 13/00* (2006.01)
(Continued)

(52) U.S. Cl.
CPC ........ *A61M 16/1095* (2014.02); *A61M 13/00* (2013.01); *A61M 13/003* (2013.01);
(Continued)

(58) Field of Classification Search
CPC .......... A61B 18/14; A61B 2017/00482; A61B 2018/00166; A61B 2018/00178;
(Continued)

(56) References Cited

U.S. PATENT DOCUMENTS 2,728,337 A * 12/1955 Guillemin, Jr. .......... A61B 5/01
219/520
3,438,253 A * 4/1969 Kuether .................. G01F 1/698
73/170.12
(Continued)

FOREIGN PATENT DOCUMENTS

DE 19545719 A1 6/1997
GB 817325 A * 7/1959

OTHER PUBLICATIONS

Rolf Isermann, "Mechatronisch Systeme" 1999, 2002, 2008, 9 pages and translation thereof.

*Primary Examiner* — Annette Dixon
(74) *Attorney, Agent, or Firm* — Stuart H. Mayer; Kaplan Breyer Schwarz LLP

(57) ABSTRACT

A method is provided for controlling the gas temperature in medical devices by means of a state observer, e.g., in the field of laparoscopy or respiration, and to devices for carrying-out said method.

6 Claims, 9 Drawing Sheets

(51) Int. Cl.
*A61M 16/08* (2006.01)
*G05D 23/19* (2006.01)

(52) U.S. Cl.
CPC ..... *A61M 16/0875* (2013.01); *G05D 23/1917* (2013.01); *A61M 2202/0208* (2013.01); *A61M 2202/0225* (2013.01); *A61M 2205/3368* (2013.01); *A61M 2205/3653* (2013.01); *A61M 2205/50* (2013.01)

(58) Field of Classification Search
CPC .......... A61B 2018/00666; A61B 2018/00678; A61B 2018/00708; A61B 2018/00791; A61B 2018/00797; A61B 2018/00815; A61B 2018/00821; A61B 2018/00988; A61B 2562/08; A61B 5/028; A61B 5/1495; A61B 5/6855; A61B 5/6856; A61B 5/6857; A61M 13/003; A61M 16/0012; A61M 16/0051; A61M 16/0066; A61M 16/0069; A61M 16/024; A61M 16/026; A61M 16/0465; A61M 16/0666; A61M 16/0841; A61M 16/0875; A61M 16/1075; A61M 16/1085; A61M 16/109; A61M 16/1095; A61M 16/16; A61M 16/161; A61M 2016/0039; A61M 2205/3368; A61M 2205/3372; A61M 2205/3653; A61M 2205/7518; A61M 2205/7536; A61M 2205/7545; A61M 2205/8206; G05D 23/2401; G06F 30/20; H01M 10/482; H01M 10/486; H01M 10/613; H01M 10/633; H02P 21/141; Y02E 60/10

See application file for complete search history.

(56) References Cited

U.S. PATENT DOCUMENTS

| | | | |
|---|---|---|---|
| 3,789,190 A | | 1/1974 | Orosy |
| 4,014,382 A | * | 3/1977 | Heath .................. A61M 16/12 165/60 |
| 5,411,474 A | * | 5/1995 | Ott ...................... A61M 13/003 600/560 |
| 5,553,622 A | * | 9/1996 | McKown ............... A61B 5/028 600/505 |
| 2002/0000783 A1 | * | 1/2002 | Maceratini ........... H02P 21/141 318/727 |
| 2009/0306528 A1 | * | 12/2009 | Curti .................... A61B 5/0878 600/537 |
| 2010/0312416 A1 | | 12/2010 | Demirdelen |
| 2013/0073013 A1 | * | 3/2013 | Pujol .................. A61M 16/024 607/104 |
| 2014/0050951 A1 | * | 2/2014 | Fleckenstein ....... H01M 10/633 429/62 |
| 2014/0166005 A1 | * | 6/2014 | Tatkov .............. A61M 16/0012 128/203.14 |
| 2014/0200559 A1 | * | 7/2014 | Doyle, III .............. G16H 20/17 604/891.1 |
| 2017/0147781 A1 | * | 5/2017 | Gondhalekar ...... A61M 5/1723 |

* cited by examiner

Fig. 3

Equation 1

$$dQ_3 = \alpha(\vartheta - \sigma) \cdot dA \cdot dt$$

Equation 2

$$dQ_{Dr} = \rho_{Dr} \cdot dV_{Dr} \cdot c_{Dr} \cdot \frac{\partial \sigma}{\partial t} dt$$

$$\Leftrightarrow dQ_{Dr} = \rho_{Dr} \cdot dA_{Dr} \cdot dx \cdot c_{Dr} \cdot \frac{\partial \sigma}{\partial t} dt$$

Equation 3

$$dQ_{el} = \frac{P_{el} \cdot dt \cdot dx}{l_{HZ}}$$

Equation 4

$$dQ_{Dr} = dQ_3 + dQ_{el}$$

Equation 5

$$\dot{\sigma} = -\frac{\alpha \cdot \pi \cdot d_{Dr}}{\rho_{Dr} \cdot A_{Dr} \cdot c_{Dr}} \cdot \sigma + \frac{\alpha \cdot \pi \cdot d_{Dr}}{\rho_{Dr} \cdot A_{Dr} \cdot c_{Dr}} \cdot \vartheta + \frac{1}{2 \cdot \rho_{Dr} \cdot A_{Dr} \cdot c_{Dr} \cdot l_{HZ}} \cdot P_{el}$$

Equation 6 (comparison)

$$\dot{x} = -A \cdot x + B \cdot u + E \cdot d$$

Fig. 4

$$\begin{bmatrix} \dot{\vartheta} \\ \dot{\sigma} \\ \dot{\eta} \end{bmatrix} = \begin{bmatrix} \dfrac{-\left(\pi \cdot (2 \cdot \alpha \cdot d_{Dr} + \beta \cdot d_{St}) + \dfrac{\dot{V}}{A_{Str} \cdot l_{Hz}}\right)}{\rho_F \cdot A_{Str} \cdot c_F} & \dfrac{2 \cdot \alpha \cdot \pi \cdot d_{Dr}}{\rho_F \cdot A_{Str} \cdot c_F} & \dfrac{\beta \cdot \pi \cdot d_{St}}{\rho_F \cdot A_{Str} \cdot c_F} \\ \dfrac{\alpha \cdot \pi \cdot d_{Dr}}{\rho_{Dr} \cdot A_{Dr} \cdot c_{Dr}} & -\dfrac{\alpha \cdot \pi \cdot d_{Dr}}{\rho_{Dr} \cdot A_{Dr} \cdot c_{Dr}} & 0 \\ \dfrac{\beta \cdot \pi \cdot d_{St}}{\rho_S \cdot A_S \cdot c_S} & 0 & \dfrac{-\pi \cdot (\beta \cdot d_{St} + \gamma \cdot d_{Sa})}{\rho_S \cdot A_S \cdot c_S} \end{bmatrix} \cdot \begin{bmatrix} \vartheta \\ \sigma \\ \eta \end{bmatrix}$$

$$+ \begin{bmatrix} 0 & 0 & 0 \\ 0 & \dfrac{1}{2 \cdot \rho_{Dr} \cdot A_{Dr} \cdot c_{Dr} \cdot l_{Hz}} & 0 \\ 0 & 0 & 0 \end{bmatrix} \cdot \begin{bmatrix} 0 \\ P_{el} \\ 0 \end{bmatrix}$$

$$+ \begin{bmatrix} \dfrac{\dot{V}}{A_{Str} \cdot l_{Hz}} & 0 & 0 \\ 0 & 0 & 0 \\ 0 & 0 & \dfrac{\gamma \cdot \pi \cdot d_{Sa}}{\rho_S \cdot A_S \cdot c_S} \end{bmatrix} \cdot \begin{bmatrix} \vartheta_E \\ 0 \\ \xi \end{bmatrix}$$

31 °C ambient

21 ° ambient + fan

METHOD AND DEVICE FOR CONTROLLING THE TEMPERATURE OF THE GAS FLOW IN MEDICAL DEVICES

BACKGROUND OF THE INVENTION

The present invention relates to a method for controlling the gas temperature in medical devices, e.g. in the field of laparoscopy or respiration, and to devices for carrying-out said method.

In various medical procedures, gases are introduced into the inward parts of the body. An example thereof is the laparoscopy, wherein up to now during a therapeutic intervention gases (e.g., $CO_2$) are supplied to the abdomen. In these procedures the supplied gas is normally heated, so that the gas entering into the inward parts of the body has nearly body temperature, since too cold as well as too hot gases would lead to pain symptoms of the patient. Therefore, measurement and control of the gas temperature are particularly important. Typically, the gas lines used for such procedures are provided with temperature sensors that are intended to allow a corresponding temperature control. The use of such separate sensors is disadvantageous, among other reasons, since they cause additional cost. Since the associated hoses are disposable articles, it is desirable to avoid any additional cost. Another possibility of measuring the temperature is the measurement of the temperature of the heating wire. There is a relationship between the gas temperature at the exit of the hose and the temperature of the heating wire, it is however dependent on a number of parameters, such as, e.g., the volume flow of the gas, the type of gas, the heating power, the geometry, and the material of the hose, as well as the outside temperature, just to name some of these factors.

SUMMARY OF THE INVENTION

The method according to the invention is based, substantially, on that for measuring and controlling the gas temperature at the patient-side end of a heating hose, a mathematical model is used. For this purpose, the complete system consisting of heating wire, electronic measurement system, supply line, temperature sensor, and gas flow is described by a set of differential equations and put together in a so-called state-space model. Under the condition that the parameters of the model are sufficiently precisely determined, then, with identical input variables, an estimation for the gas temperature at the exit of the gas hose (i.e. trocar entry) can be made. By comparison of the actual and the estimated wire temperature, deviations (so-called observer errors) can be detected. They may occur, e.g., due to different initial states (e.g., there is no a priori information about the gas temperature at the beginning of the gas supply). If the observer error is rated with a performance criterion, and the result is then fed back to the model (state-variables correction), the error will go down, and as a result, a precise estimate for the gas temperature at the exit of the hose is obtained. The advantage of the proposed method is, among others, that for the measurement of the gas temperature at the exit of the hose, no additional temperature sensor is required. As a result, even without a temperature sensor at the exit of the hose, a precision of estimation is achieved that is comparable to the precision of measurement by means of a conventional hose including a temperature sensor. Safety for the patients is thus ensured even without an additional sensor.

Preferably, the method according to the invention is configured such that the estimation system is implemented as a state observer, in particular as a Luenberger observer. Such state observers including the Luenberger observer are described, e.g., in textbooks of control engineering.

A particular embodiment of such a device implementing the above method is an insufflation apparatus for laparoscopy. It comprises a gas supply (e.g., from a pressure bottle) that is provided with the required exit pressure, and is enabled to achieve a suitable volume flow. The volume flow is controllable, e.g., between 0 and 50 l/min. Through a supply hose, the gas is introduced into the inward parts of the body. For obtaining the desired temperature (approx. body temperature, i.e., approx. 37° C.) at the exit of the hose, there is provided a heating device, e.g., a heating wire, in the interior of the hose. The gas introduced into the inward parts of the body may be discharged either through separate gas exit devices, through a suction apparatus or also simply through leaks from the inward parts of the body. By the above method according to the invention, using the measurement data from the heating wire (by means of resistance measurement), the actual temperature at the exit of the hose is estimated and is controlled by variation of the heating power of the heating wire. Using a separate temperature sensor is not necessary: when using a heating wire the resistance of which is temperature-dependent, the measurement of the heating wire temperature can be made by a resistance measurement, so that no additional components are required.

An alternative embodiment of the invention comprises a respiratory apparatus. By the respiratory apparatus, oxygen or an oxygen-containing gas mixture is led into the lung of the patient. For respiration, wetting of the oxygen-containing gas mixture is absolutely necessary. For preventing condensation, as well as for obtaining a gas temperature that is acceptable for the patient, a resistance heating by an electrical heating wire is provided within the respiration hose. In an analogous manner as in the above device for laparoscopy, the heating wire can serve as a temperature sensor by using a corresponding resistance measurement. The actual temperature at the exit of the hose is estimated by the method according to the invention. By means of the estimated value, the heating power is electronically controlled. As a result, a device is obtained that ensures a precise measurement and control of the gas temperature at the entrance of the hose, even under most various respiration conditions.

BRIEF DESCRIPTIONS OF THE DRAWINGS

Embodiments of the invention are shown in the figures and are explained in more detail in the following:

FIG. 1 shows in a model representation a gas supply hose with an incorporated heating wire, wherein the reference numerals have the following meanings:

| | |
|---|---|
| 1.1 | volume flow |
| 1.2 | $\vartheta_E$ gas entry temperature |
| 1.3 | observed heating wire control volume |
| 1.4 | $\xi$ ambient temperature |
| 1.5 | observed fluid control volume |
| 1.6 | $\eta$ hose temperature |
| 1.7 | $\sigma(R_{Dr})$ wire temperature |
| 1.8 | $\vartheta$ gas exit temperature |
| 1.9 | unheated length |
| 1.10 | heated length |
| 1.11 | observed hose control volume |

| | |
|---|---|
| 1.12 | exchanged amounts of heat |
| 1.13 | $U_{Dr}$ heating voltage |

FIG. 2 (from Isermann R (2008), Mechatronische Systeme, Grundlagen Springer-Verlag: Berlin) shows schematically the estimation process according to the invention. Control of the heating wire is performed, for instance, by a pulse-wide-modulated voltage (PWM).

FIG. 3 shows exemplarily the procedure for describing the behavior of the wire temperature over time.

FIG. 4 shows the resulting state-space model, which is dependent on the gas flow.

Figure 6:
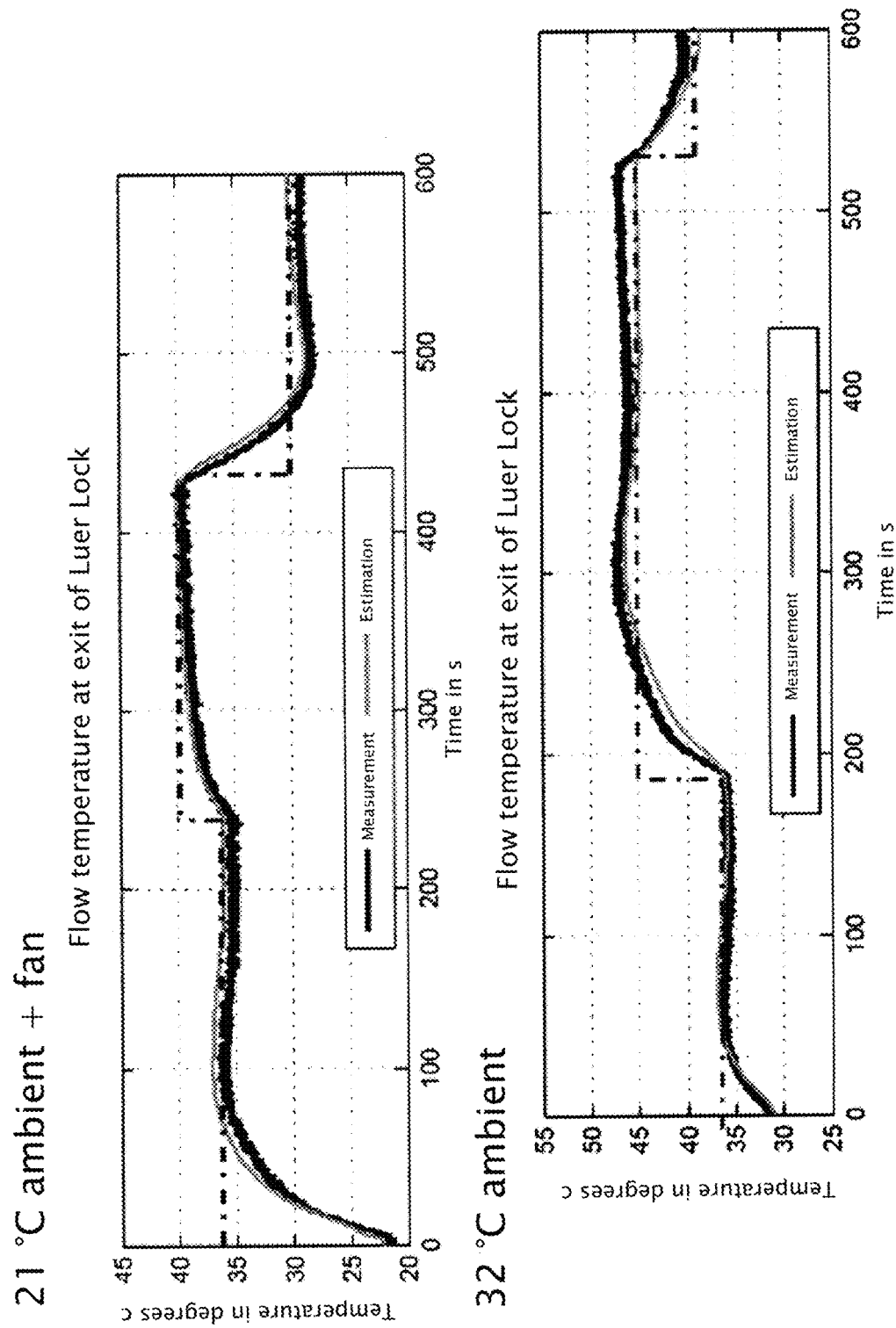
Figure 7A:
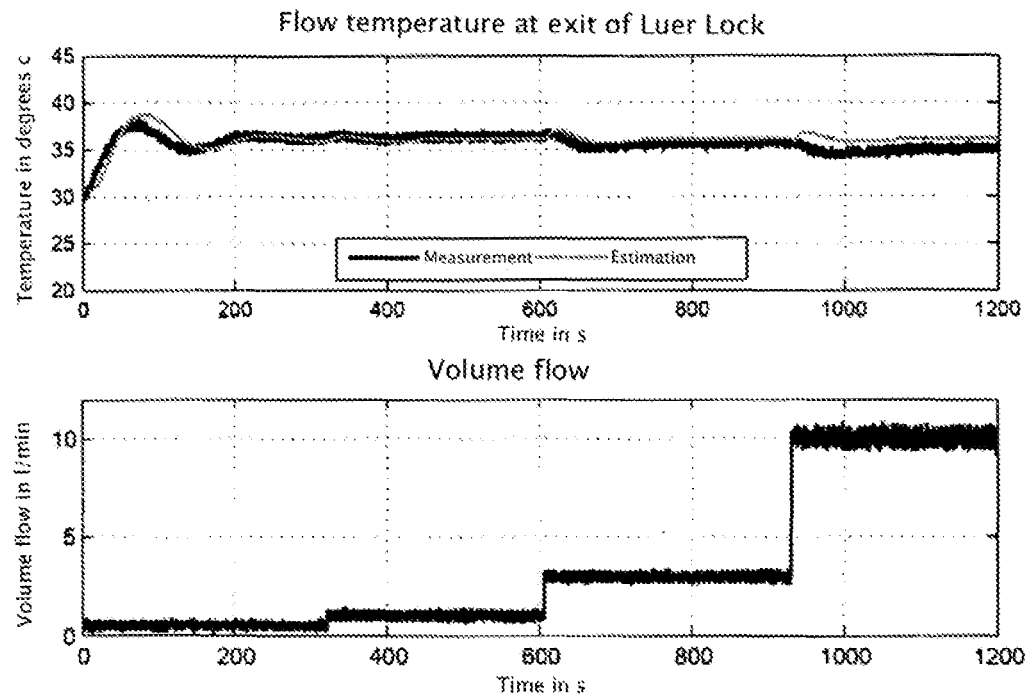
Figure 7B:
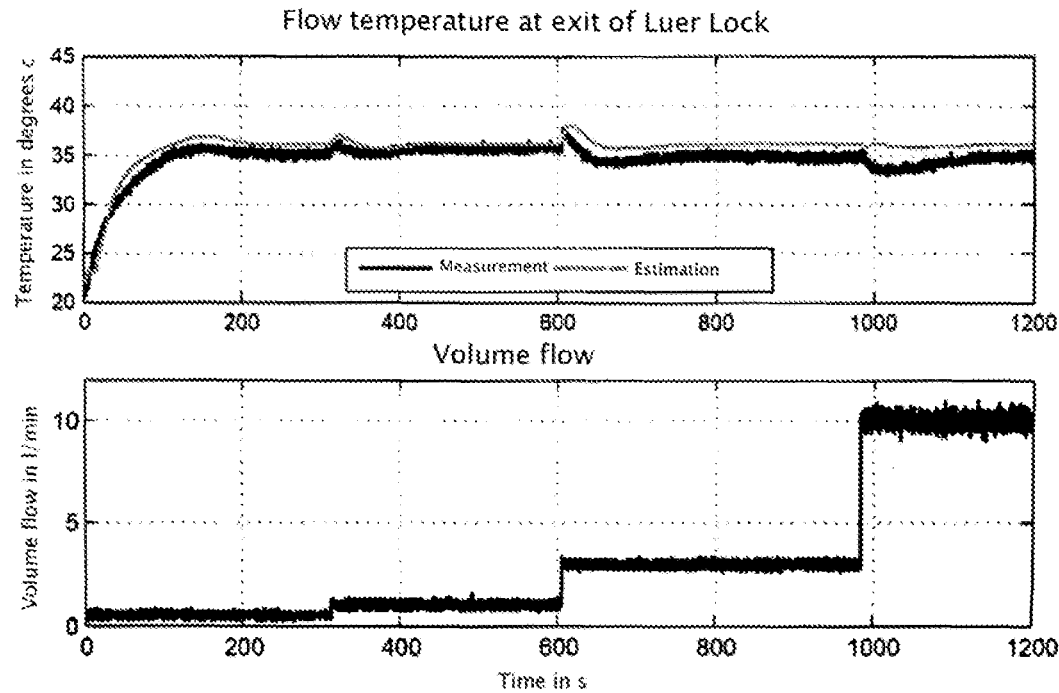

FIGS. 6 and 7 show the method for different ambient conditions that were modeled as a disturbance. The real application is subjected to a series of disturbances, such as, e.g., a different ambient temperature ($\xi$ in FIG. 4) or a different gas entry temperature ($\vartheta_E$ in FIG. 4). The disturbances are provided in the state-space model. It can be seen a high agreement of the measured temperature with the estimated temperature, even with variation of the flow rate.

Figure 8:
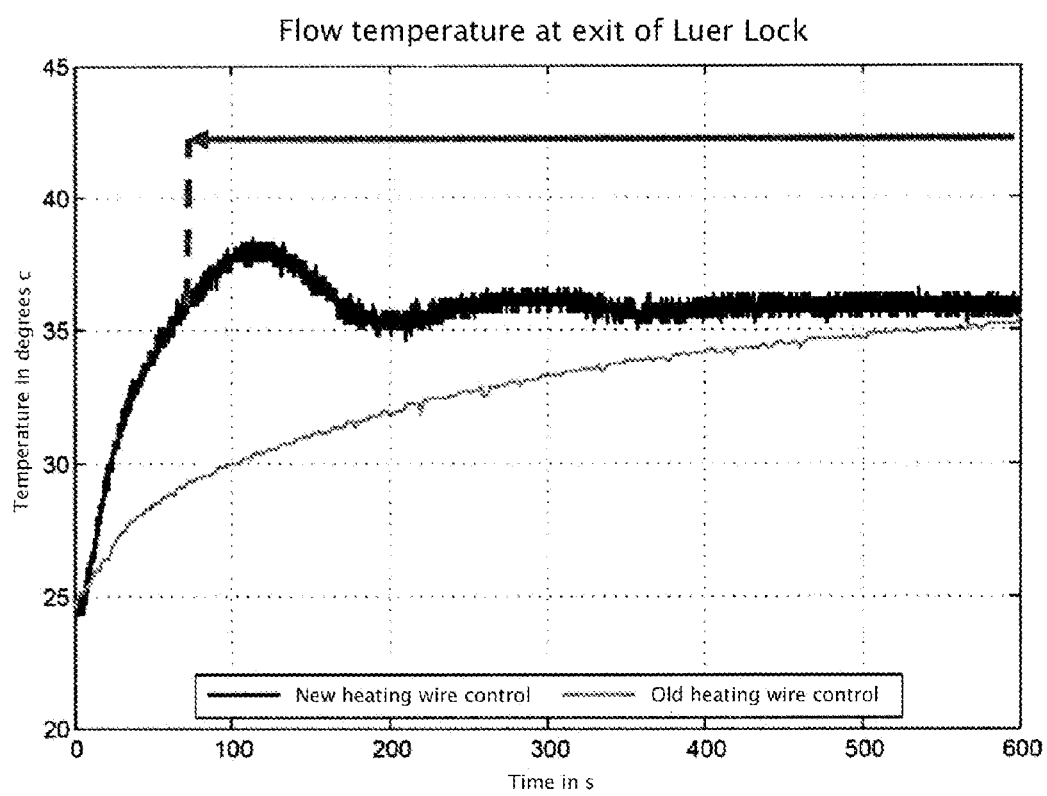

FIG. 8 shows a comparison of the heating wire control according to the invention to a classic pre-control that only adjusts the power of the heating wire by the resistance of the heating wire. As a result, it can be seen that the method according to the invention can achieve the control very much faster.

Figure 9:
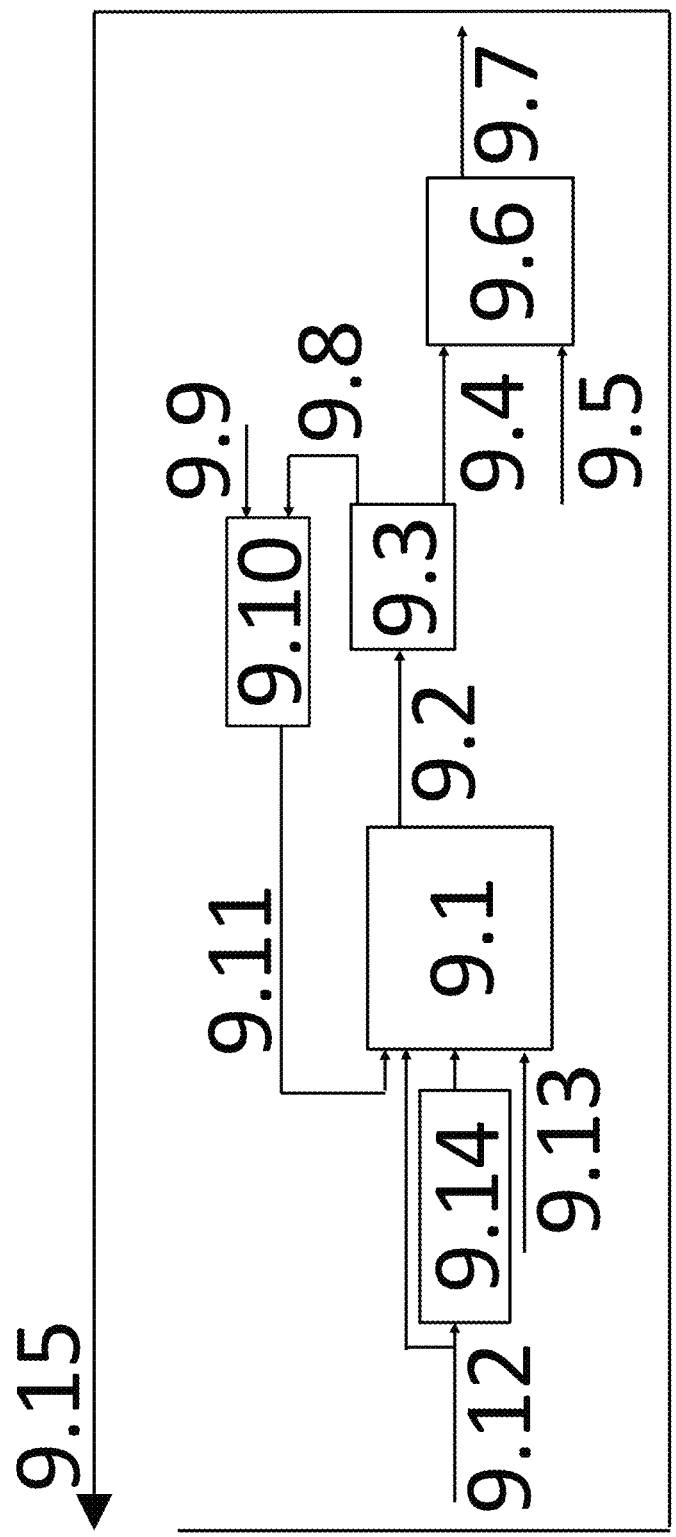

FIG. 9 shows a sequence diagram of a software module, wherein the reference numerals have the following meanings:

| | |
|---|---|
| 9.1 | numerical solution of the observer differential equation |
| 9.2 | estimated state variables |
| 9.3 | separation of the state variables |
| 9.4 | estimated gas exit temperature |
| 9.5 | reference value for gas exit temperature |
| 9.6 | controller |
| 9.7 | heating wire voltage |
| 9.8 | estimated wire temperature |
| 9.9 | measured wire temperature |
| 9.10 | calculation observer error |
| 9.11 | observer error |
| 9.12 | measured volume flow |
| 9.13 | measured electrical power |
| 9.14 | calculation correction vector |
| 9.15 | numerical calculation: i = i + 1 |

DETAILED DESCRIPTION OF THE INVENTION

A gas volume flow flows through the hose in the direction of the arrow. However, corresponding to the length of the heating wire, in this model, only a partial length of the hose is heated. Then follow an unheated remaining length and a Luer adapter for the transition to the patient. Measured is herein the temperature of the heating wire by resistance measurement. The temperature of the flow at the exit from the hose is to be measured for volume flows from 0 to 50 l/min in a range from 32° C. to 42° C.

Figure 2:
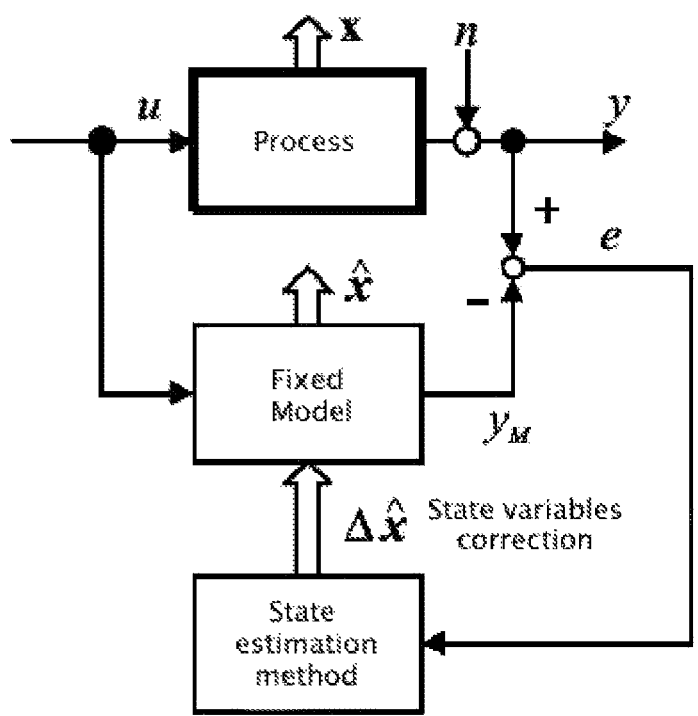

In this method, the volume flow, the temperature of the heating wire, the electrical power and the time courses thereof are continuously measured and processed. FIG. 2 (from Isermann R (2008). Mechatronische Systeme. Grundlagen. Springer-Verlag: Berlin) shows schematically the estimation process according to the invention. Control of the heating wire is performed, for instance, by a pulse-wide-modulated voltage (PWM). The electrical power (U in FIG. 2) and the wire resistance (Y in FIG. 2) are measured. The measurement data are subjected to a mathematical model ("fixed model" in FIG. 2), which illustrates the dynamic behavior of the system. For various flows, different model parameters are provided, so that the model can be adapted to the measured volume flow. The temperature value estimated by means of the model is compared to the measured actual value of the wire temperature ($y-y_M$ in FIG. 2). Deviations between the estimated value and the measured value (e in FIG. 2) are fed back to the model such that the estimation of the state variables is improved (state estimation method in FIG. 2). Once the estimate matches the actual value, the estimated state variables ($\hat{x}$ in FIG. 2) can be taken and further utilized. One of these state variables is the exit temperature of the gas flow, which consequently can precisely be estimated.

The method according to the invention presents a number of advantages. The observed temperature/state variable considers disturbances of the process (disturbance observer). The observed variable can be used as a control variable, so that the adjustment of different reference values is possible. Overall, a control performance will result that is comparable to the possible control performance when using a temperature sensor (for measurement of the flow temperature). A risk for the patient is thereby widely excluded, and the control process can be configured, by the omission of the flow temperature sensor, in a considerably more economic way. A particular advantage of the method according to the invention is that errors due to defective flow temperature sensors are excluded. Since in this method, sensor and actor are identical, there will fail, in case of a defect, both the measuring element and the actuator. Introducing heating power without a simultaneous verification by a temperature measurement is not possible.

Figure 1:
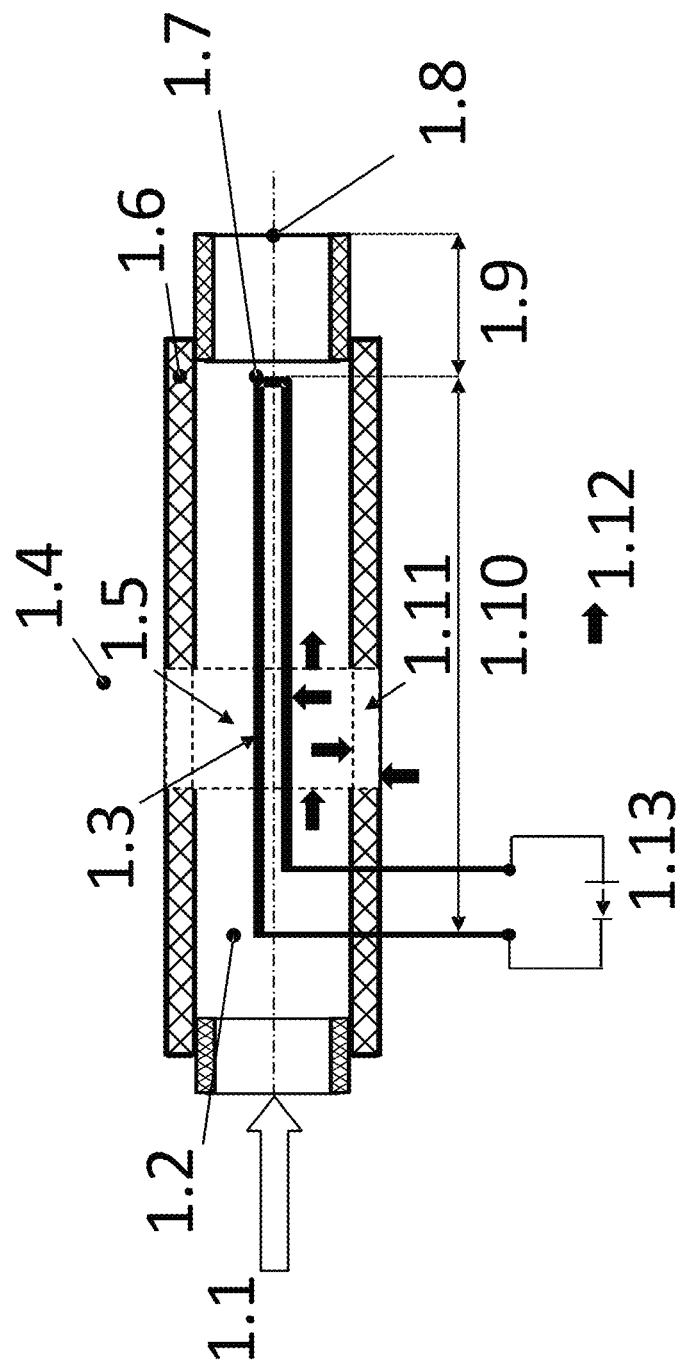

For the estimation of the state variable (exit temperature), a mathematical model of the process is required. This mathematical model has a standardized form, called state-space model, which is represented in FIG. 4. For determining this state-space model, it is necessary to build-up a physical replacement model of the process and to bring it into this standardized form. The employed matrices have to be provided with values (identification). The procedure for describing the behavior of the wire temperature over time is shown exemplarily in FIG. 3, wherein the amount of heat exchanged between fluid and wire (equation 1), the amount of heat stored in the wire (equation 2), and the supplied amount of heat (equation 3) are described in the form of differential equations. Equation 4 then shows the energy balance (heat balance). By combining the equations and suitable operations thereon, equation 5 is obtained. Equation 6 shows as a comparison the applied state-space model, which is widely identical with equation 6, and coefficients of which contain the parameters of the model equations. A corresponding procedure is followed for modeling the gas and hose temperature (cf. FIG. 1).

FIG. 4 shows the resulting state-space model, which is dependent on the gas flow.

Figure 5:
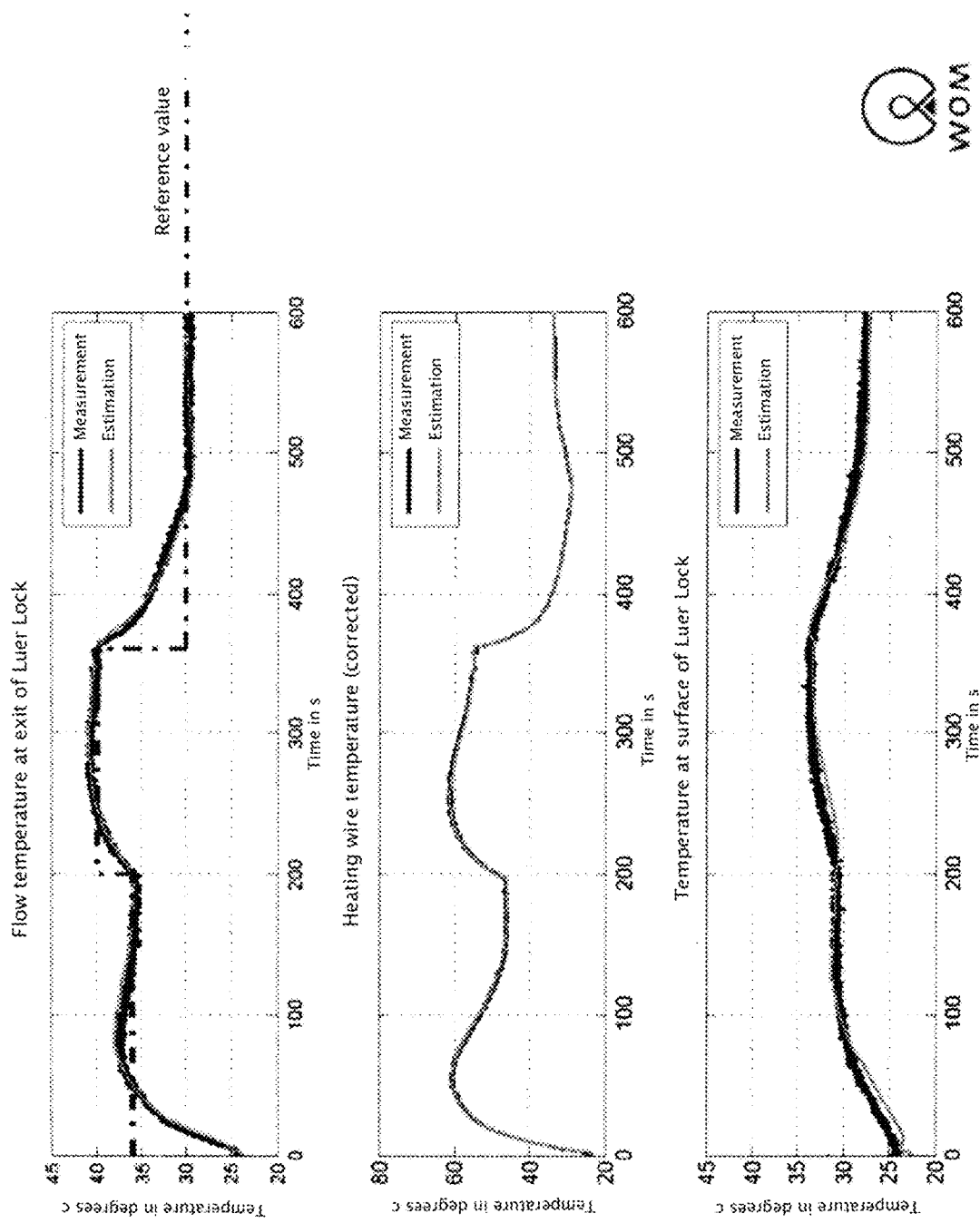
FIG. 5 shows the comparison of the actually measured data to the estimated data obtained by means of the method. As a result, it is shown that the applied model is correct and leads to the necessary precision of the estimated data.

FIG. 5 shows the comparison of the actually measured data to the estimated data obtained by means of the method. As a result, it is shown that the applied model is correct and leads to the necessary precision of the estimated data.

FIGS. 6 and 7 show the method for different ambient conditions that were modeled as a disturbance. The real application is subjected to a series of disturbances, such as, e.g., a different ambient temperature ($\xi$ in FIG. 4) or a different gas entry temperature ($\vartheta_E$ in FIG. 4). The disturbances are provided in the state-space model. It can be seen a high agreement of the measured temperature with the estimated temperature, even with variation of the flow rate.

FIG. 8 shows a comparison of the heating wire control according to the invention to a classic pre-control that only adjusts the power of the heating wire by the resistance of the heating wire. As a result it can be seen that the method according to the invention can achieve the control very much faster.

The practical implementation of the above method is suitably achieved on a microcontroller that is part of the medical device. It is typically provided with inputs and out-puts and memories. The mathematical operations are performed in the form of a software module. A sequence diagram of the software module is shown in FIG. 9, wherein the reference numerals have the following meanings:

| | |
|---|---|
| 9.1 | numerical solution of the observer differential equation |
| 9.2 | estimated state variables |
| 9.3 | separation of the state variables |
| 9.4 | estimated gas exit temperature |
| 9.5 | reference value for gas exit temperature |
| 9.6 | controller |
| 9.7 | heating wire voltage |
| 9.8 | estimated wire temperature |
| 9.9 | measured wire temperature |
| 9.10 | calculation observer error |
| 9.11 | observer error |
| 9.12 | measured volume flow |
| 9.13 | measured electrical power |
| 9.14 | calculation correction vector |
| 9.15 | numerical calculation: i = i + 1 |

The software can be included on an own memory chip, e.g. an EPROM.

Those skilled in the art can, based on the present description including the figures and the technical literature known at the time of the application, implement further embodiments of the invention, without any further inventiveness being required.

The invention claimed is:

1. A method for measuring and controlling the gas temperature in an insufflator for laparoscopy,
    wherein a gas is supplied by a gas supply device by means of a supply line to a patient, wherein a gas volume flow is controllable, between 0 and 50 l/min,
    wherein the gas is heated from room temperature to a desired temperature of 32-42° C. within the gas supply hose,
    wherein when changing the gas volume flow, a time span until the desired temperature is reached is a maximum of 100s,
    wherein heating occurs by a heating wire,
    wherein a temperature measurement is made by measuring a resistance of the heating wire such that the heating wire used for heating and for performing the temperature measure are a single element,
    wherein the heating power of the heating wire is electrically controlled, further comprising
    the resistance of the heating wire is an input variable of a mathematical estimation system, which mathematically describes a state space, which estimates the actual temperature at the exit of the hose and controls the heating power of the heating wire by means of this estimated value, wherein the mathematical estimation system is configured as a Luenberger observer.

2. The method according to claim 1, wherein the gas is $CO_2$ or an oxygen-containing gas mixture.

3. The method of claim 1 wherein the gas is heated from room temperature to the desired temperature of 37° C. within the gas supply hose.

4. The method of claim 1, wherein control of the heating wire is performed by a pulse-wide-modulated voltage.

5. An insufflator for laparascopy for supplying gases to patients comprising a gas supply device, a gas supply hose, a heating wire in the supply hose, characterized by that the devices are provided for carrying-out a method according to claim 1.

6. An insufflator for laparascopy according to claim 5, wherein at least one microprocessor, at least one memory, and at least one software, which are provided for carrying-out a method according to claim 1.

* * * * *